US00PP12679P2

(12) United States Plant Patent
Breier

(10) Patent No.: US PP12,679 P2
(45) Date of Patent: Jun. 4, 2002

(54) PETUNIA PLANT NAMED 'BREVT'

(75) Inventor: Ilan Breier, Beni Zion (IL)

(73) Assignee: Breier & Son Ltd., Beni Zion (IL)

( * ) Notice: Subject to any disclaimer, the term of this patent is extended or adjusted under 35 U.S.C. 154(b) by 0 days.

(21) Appl. No.: 09/592,380

(22) Filed: Jun. 12, 2000

(51) Int. Cl.[7] ..... A01H 5/00
(52) U.S. Cl. ..... Plt./356
(58) Field of Search ..... Plt./356

(56) References Cited

PUBLICATIONS

UPOV–ROM GTITM Computer Database, 2000/6, GTI Jouve Retrieval Software, citation for 'Brevt'.*

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Petunia plant named 'Brevt', characterized by its uniform cascading plant habit; freely and continuous branching; and numerous blue purple and white bi-colored flowers.

1 Drawing Sheet

BACKGROUND OF THE INVENTION

The present Invention relates to a new and distinct cultivar of Petunia plant, botanically known as *Petunia×hybrida*, and hereinafter referred to by the cultivar name Brevt.

The new Petunia is a product of a planned breeding program conducted by the Inventor in Beni Zion, Israel. The new Petunia originated from a cross made by the Inventor of a Petunia selection identified as K-27, not patented, as the female, or seed, parent with a Petunia selection identified as K-51, not patented, as the male, or pollen, parent. The new Petunia was selected by the Inventor in 1997 on the basis of its bi-colored flowers.

Asexual reproduction of the new cultivar by terminal cuttings taken in Poland since 1998, has shown that the unique features of this new Petunia are stable and reproduced true to type in successive generations.

SUMMARY OF THE INVENTION

Plants of the cultivar Brevt have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Brevt'. These characteristics in combination distinguish 'Brevt' as a new and distinct cultivar:

1. Uniform cascading plant habit.
2. Freely and continuous branching.
3. Numerous blue purple and white bi-colored flowers.

Plants of the new cultivar differ primarily from plants of the parent selections in flower color.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which more accurately describe the actual colors of the new Petunia. The photograph comprises a side perspective view of typical flowering plants of 'Brevt' grown in a window box.

DETAILED BOTANICAL DESCRIPTION

In the following description, color references are made to The Royal Horticultural Society Colour Chart except where general terms of ordinary dictionary significance are used. Plants grown in containers were used for the following description. Plants were grown under conditions which closely approximate commercial production conditions in Beni Zion, Israel, during the spring in a greenhouse and were about 3 months old.

Botanical classification: *Petunia×hybrida* cultivar Brevt.

Parentage:

*Female parent.*—*Petunia×hybrida* selection identified as K-27, not patented.

*Male parent.*—*Petunia×hybrida* selection identified as R-51, not patented.

Propagation:

*Type cutting.*—Terminal vegetative cuttings.

*Time to initiate roots, summer.*—About 12 days at 25° C.

*Time to initiate roots, winter.*—About 16 days at 20° C.

*Time to develop roots, summer.*—About 20 days at 25° C.

*Time to develop roots, winter.*—About 24 days at 20° C.

*Root description.*—Numerous, fine, fibrous and well-branched.

Plant description:

*Form.*—Annual flowering plant; initially upright, then cascading; uniform; plants eventually becoming spherical in shape. Viscid, glandular pubescent. Freely continuous basal branching with lateral branches potentially forming at every node.

*Usage.*—Appropriate for hanging baskets, window boxes and patio containers.

*Crop time.*—About 8 weeks are required to produce finished flowering plants in 10-cm containers.

*Plant height (from soil level to top of plant plane).*—About 28 cm.

*Plant length (from soil level to lateral branches apices).*—About 70 cm.

*Plant spread.*—About 60 cm.

*Vigor.*—Moderate to vigorous.

*Stem description.*—Main branches, length: About 70 cm. Main branches, diameter: About 4 mm. Lateral branches, diameter: About 2 mm. Internode length: About 3.5 cm. Texture: Dense, white, viscid and glandular pubescence. Color: 144B.

*Foliage description.*—Leaves simple, small, generally symmetrical and long persisting. Arrangement: Alternate. Length: Basal leaves, about 6 cm; middle leaves, about 4.7 cm. Width: Basal leaves, about 4.5 mm; middle leaves, about 2.7 mm. Shape: Ovate to rotund. Apex: Rounded. Base: Attenuate. Margin: Entire. Aspect: Mostly flat to slightly curved. Texture: Somewhat fleshy; glandular; slightly leathery; white pubescence, dense. Color: Young foliage, upper surface: 146A to 146B. Young foliage, lower surface: 146C. Mature foliage, upper surface: 146A; veins, 146B to 146C. Mature foliage, lower surface: 146B; veins, 146C to 146D. Petiole length: About 1 cm. Petiole diameter: About 2 mm. Petiole color: 146C to 146D.

Flower description:

*Flower type and habit.*—Large salverform flowers; flowers face upright and outwardly; single, axillary. Flowers persistent. Freely flowering.

*Natural flowering season.*—Long day responsive; spring until frost in the autumn; flowering continuous.

*Flower longevity on the plant.*—About one week.

*Flower size.*—Diameter: About 6 cm. Depth (height): About 4 cm. Tube length: About 3.2 cm. Throat diameter, distal end: About 1.5 cm. Tube diameter, proximal end: About 6 mm.

*Flower buds* (*just showing color*).—Length: About 3.5 cm. Diameter: About 6.6 mm. Shape: Oblong. Color: Apex, 86A; base, 79B.

*Corolla.*—Arrangement/appearance: Single whorl of five petals, fused into flared trumpet. Petal length from throat: About 3.1 cm. Petal width: About 2.5 cm. Petal shape: Roughly spatulate with obtuse apex. Petal margin: Entire, slightly undulate. Petal texture: Smooth, satiny. Color: Purple and white bi-colored; white margin about 3 to 7 mm in width. Petal, upper surface, when opening: 83A with white, 155D, margin. Petal, lower surface, when opening: 83A to 83B with white, 155D, margin. Petal, upper surface, opened flower: 83A with white, 155D, margin; main veins, 79A. Petal, lower surface, opened flower: 83C with white, 155D, margin; main veins, 166A. Flower throat (inside): 79D; veins, 79A. Flower tube (outside): 79A to 79B; veins, 79D; white dense pubescence.

*Sepals.*—Arrangement/appearance: Single whorl of five sepals, star-shaped. Length: About 1.9 cm. Width: About 5 mm. Shape: Elliptic, undulating. Apex: Obtuse. Margin: Entire. Texture: Dense pubescence. Color: Upper surface: 146A. Lower surface: 146B.

*Peduncles.*—Length: About 3.1 cm. Width: About 1.75 mm. Strength: Flexible and wiry, holding flowers upright and outwardly. Texture: Dense pubescence. Color: 146A with slight anthocyanin, 166A to 166B.

*Reproductive organs.*—Stamens: Quantity: About five. Anther shape: Four-parted, oval. Anther length: About 2.5 mm. Anther color: 158A. Pollen amount: Moderate. Pollen color: 158A. Pistils: Quantity: One. Pistil length: About 2 cm. Stigma shape: Oval. Stigma color: Immature, 144A; mature, 144B. Style length: About 1.4 cm. Style color: 145C. Ovary color: 144C.

*Seed.*—Seed production has not been observed.

Disease resistance: Plants of the new Petunia have not been noted to be resistant to pathogens common to Petunia.

Weather tolerance: Plants of the new Petunia have been observed to be tolerant to rain and wind.

Low temperature tolerance: Plants of the new Petunia have been observed to be tolerant to temperatures about −3° C.

It is claimed:

1. A new and distinct cultivar of Petunia plant named 'Brevt', as illustrated and described.

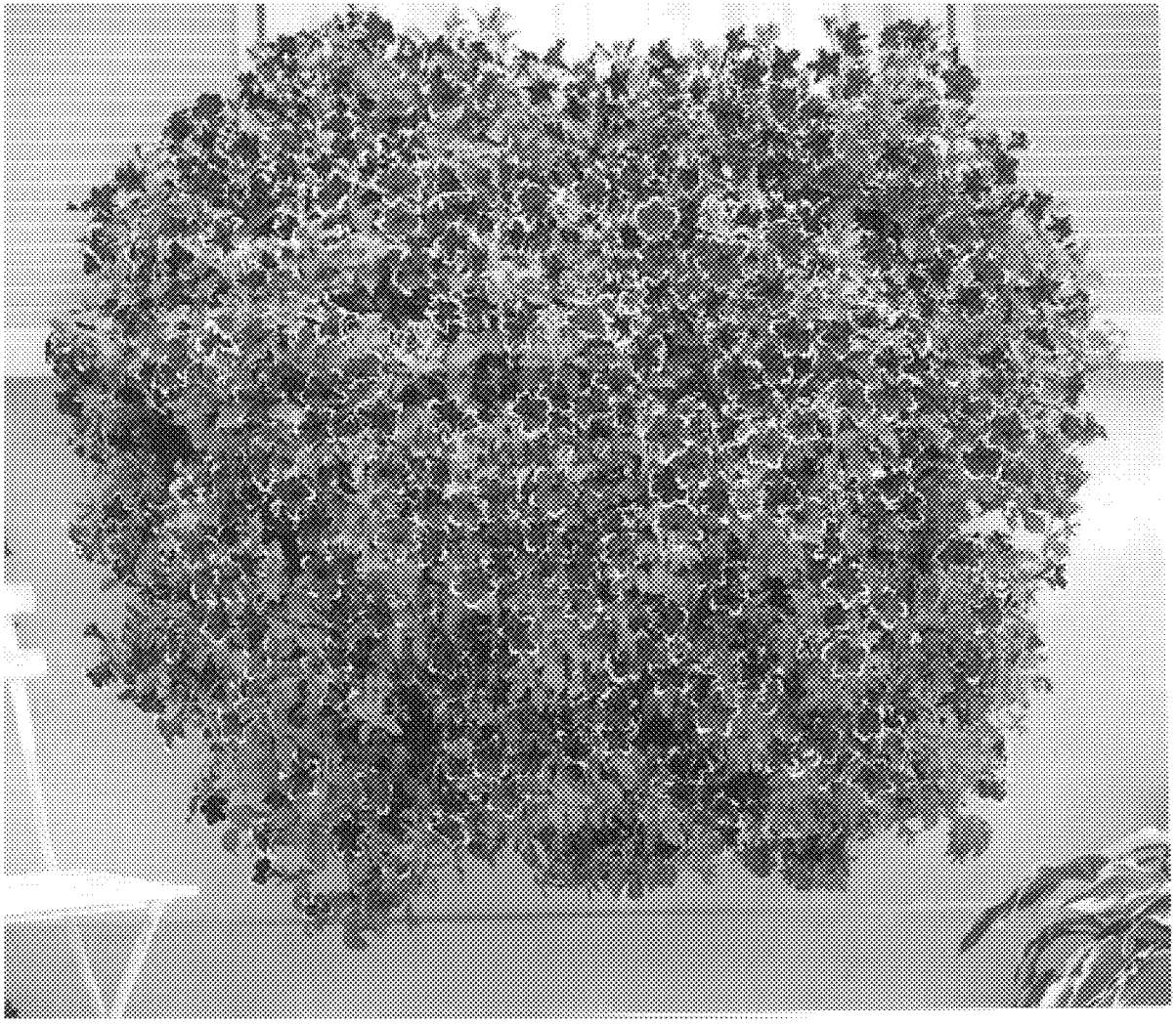

* * * * *